(12) United States Patent
Wanderman (10) Patent No.: US 10,945,652 B1
(45) Date of Patent: Mar. 16, 2021

(54) KEGEL EXERCISE MEASUREMENT AND FEEDBACK DEVICE

(71) Applicant: Steven Wanderman, Sedona, AZ (US)

(72) Inventor: Steven Wanderman, Sedona, AZ (US)

(*) Notice: Subject to any disclaimer, the term of this patent is extended or adjusted under 35 U.S.C. 154(b) by 294 days.

(21) Appl. No.: 15/999,141

(22) Filed: Aug. 17, 2018

Related U.S. Application Data (60) Provisional application No. 62/547,052, filed on Aug. 17, 2017.

(51) Int. Cl.
| | | |
|---|---|---|
| *A61B 5/22* | (2006.01) | |
| *A61B 5/00* | (2006.01) | |
| *A63B 23/20* | (2006.01) | |
| *A63B 21/002* | (2006.01) | |

(52) U.S. Cl.
CPC .......... *A61B 5/227* (2013.01); *A61B 5/4337* (2013.01); *A63B 23/20* (2013.01); *A63B 21/002* (2013.01); *A63B 2220/56* (2013.01)

(58) Field of Classification Search
CPC ..... A61B 5/227; A61B 5/4337; A61B 5/1076; A63B 23/20; A63B 2220/56; A63B 2220/51; A63B 2071/0625; A63B 2230/60; A61N 1/36007
See application file for complete search history.

*Primary Examiner* — Christine H Matthews
(74) *Attorney, Agent, or Firm* — Invention To Patent Services; Alex Hobson (57) ABSTRACT

A Kegel exercise measurement and feedback device measures the amount of force that is exerted on a sensor portion and provides feedback in the form of vibration, a phrase or a light that is emitted from a feedback module. A sensor portion comprises a resilient body having a bladder in an inner cavity that can be compressed by Kegel exercises. Air within the bladder is forced into a bellows of the measurement portion which expands the bellows and a contactor plate attached thereto. As the contactor plate moves, due to the expansion of the bellows, it makes contact with level contactors to activate a corresponding feedback phrase, emitted light or vibration. The phrases emitted may be phrases recorded by a user and stored in memory or may be pre-loaded into memory. The sensor portion may be detachable from the measurement portion of connection conduit.

21 Claims, 6 Drawing Sheets

KEGEL EXERCISE MEASUREMENT AND FEEDBACK DEVICE

CROSS REFERENCE TO RELATED APPLICATIONS

This application claims the benefit of priority to U.S. provisional application No. 62/547,052 filed on Aug. 17, 2017, the entirety of which is hereby incorporated by reference herein.

BACKGROUND OF THE INVENTION

Field of the Invention

The present invention relates to a Kegel exercise measurement and feedback device having a phrase module to emit a phrase related to the amount of pressure or force measured by the device and optionally a light module to emit a light having an intensity of frequency or flashing that is related to the amount of pressure or force measured by the device

Background

Kegel exercises are often considered taboo for discussion in various circles. However, Kegel exercises can be an effective way to strengthen the pelvic floor muscles, which can prevent urinary incontinence type issues.

SUMMARY OF THE INVENTION

The invention is directed to a Kegel exercise pressure measurement and feedback device that produces a phrase that is related to the amount of pressure exerted during the Kegel exercise, or contraction of the pelvic floor muscles. The exemplary Kegel exercise pressure measurement and feedback device (Kegel device), has a sensor portion, a connection conduit from the sensor portion to a measurement portion and a feedback module that comprises a speaker for emitting the plurality of phrases. The sensor portion is configured for insertion in the vagina and is made of an elastic material to enable compression and deformation of the resilient body and compression of a bladder therein. The air or gas within the bladder is compressed and is delivered to the measurement portion through the connection conduit. A bellows is configured within the measurement portion and expands as the bladder is compressed. A contactor plate attached to the bellows has a bellows contactor that makes electrical contact with level contactors as the bellows expands. A phrase is emitted by the phrase module that corresponds with the highest level of contactor reached by the bellows contactor. The phrase may be a pre-loaded phrase that is factory set, and/or may be a phrase that is recorded by a user and stored in memory.

An exemplary Kegel device may comprise a light module having one or more lights that emit light related to the amount of compression of the resilient body. or the highest level contactor achieved. A light module may have a single light that changes intensity or a plurality of lights, wherein the number of lights activated and/or the intensity of the light relates to the level or compression of the sensor device. In addition, one or more of the lights may be configured to flash and the frequency of flashing may be related or correspond with the level of compression of the resilient body. For example, if the first level contactor is contacted by the bellows contactor, then a single light may be activated, or the lights may flash very slowly, and if a higher level contactor is contacted by the bellows contactor, then two or more lights may be activated, or the lights may flash at a higher frequency.

An exemplary Kegel device may comprise a display configured to display a numerical value corresponding to the amount of compression of the bladder. The display may display a numerical value from 0 to 10, for example, or 0 to 100, which may indicate a percentage of full compression of the bladder. The display may be activated in any of the modes selected by the user, as described herein.

An exemplary sensor portion may comprise a bladder configured within an inner cavity of the resilient body. This interior volume of the bladder may be compressed by the resilient body and may have a controlled amount of air volume to ensure that the bellows is not over expanded, thereby causing damage. The bladder may be the inner cavity of the resilient body or may be a separate bladder within the inner cavity of the resilient body. A separate bladder within the inner cavity of the resilient body allows the outer shell to be interchangeable, and therefore change the resistance of compression. A user may interchange the outer shell to a stiffer or thicker wall thickness as they develop their pelvic floor muscles.

An exemplary measurement portion may be battery operated and may comprise the feedback module. The feedback module may however be detachably attachable to the measurement portion, or be a separate apparatus from the measurement portion. A measurement portion may comprise a wireless signal transceiver for sending and/or receiving wireless signals. The measurement portion may send a wireless signal to the feedback module and the feedback module may then emit a phrase, such as, numerical, motivational melody, and/or a clean or comical phrase, or emit alight display/show that corresponds to the level of compression of the sensor portion. or provide a corresponding numerical digital display. Numerical phrases may include numbers, perhaps 1-10, or a percentage corresponding to the compressive load applied to the sensor. A motivational melody may include clips of songs such as "Like a Virgin" by Madonna, "Slip Slidin Away" by Simon & Garfunkel, and "Satisfaction" by the Rolling Stones, pending approval by the song writer. Prerecorded phrases originating from the feedback module and corresponding to a level of compression of the measurement portion may be "clean" or "comical", encouraging, or motivational. The recordings may be factory installed or may be recorded on site by the user. Factory prerecorded phrases for very low levels of compression may include for example: "Good Start", "You Can Do Better", "Try Again", "Loose as a Goose" or "Holland Tunnel". Phrases for mid-level compression may include for example: "Nice Progress", "No Turning Back", "Lethal Weapon In Training". Phrases for high level compression may include for example: "Superb Progress", "Ouch", "Boston Strangler", "Lethal Weapon", "Danger Zone". In addition, the feedback module may emit a light display/show that corresponds to the level of compression of the sensor portion, or provide a corresponding numerical digital display The pre-recorded phrases, numerical feedback, motivational melodies, digital numeric readout, and the light display/show are designed with the dual purpose of encouraging further compression of the measurement portion and hence, strengthening of the pelvic floor muscles and secondly, for entertainment purposes. The phrases may be stored in the memory module and may be provided with the Kegel device or phrases may be recorded by a user and then indicated for a particular compression level. Personal recorded phrases may encourage a person to continue use of the Kegel device. Additionally, the feedback module may activate a vibratory component housed within the measurement device providing additional feedback to the user.

As a user of the device demonstrates quantitative increased compression, the spring may be tightened by a spring tensioning device. A spring tensioning device may pre-compress a spring by moving a plate that compresses the spring. A screw driver recess in the body of the measurement portion may enable a user to turn move the plate to compress or relax the spring. In addition, a spring may be changed for a spring having a higher or lower spring constant. An access door may allow a user to change out the spring as required to provide a full range of contact with the level contactors.

An exemplary Kegel exercise pressure measurement and feedback device may comprise a vibratory feedback module that provides a vibration stimulus to the sensor portion as a function of the amount of compression of the resilient body. The vibration feedback module may provide vibration stimulus when a threshold level of compression is reached or may provide stimulation that corresponds with an amount of compression or force exerted on the sensor portion. A low level of compression may result in a low level of vibration, having either allow frequency or amplitude and a high level of compression of the sensor portion may result in a high level of vibration, wherein the frequency of vibration and/or the amplitude of vibration is higher than at a lower level of compression. An exemplary vibration feedback module may be detachably attachable to the sensor portion, whereby an end of the sensor portion is adapted to receive a vibration feedback module. A vibration feedback module may comprise a vibration device, batteries to power the vibration device and in some cases a sensor, wireless signal receiver and or a controller. An exemplary vibration feedback module may receive sensor input regarding the amount of compression of the resilient body from a separate vibration sensor that is configured with the sensor portion or may receive a signal from a feedback module or measurement portion through a wireless signal receiver, for example. The controller of the vibration feedback module may control the level of vibration based on the signals received from the vibration sensor or from the feedback module or measurement portion. This vibration stimulus may encourage a user to strengthen their pelvic floor muscles in an effort to increase this feedback stimulus.

An exemplary Kegel exercise pressure measurement and feedback device may comprise a user interface that allows a user to select the type of feedback that is produced by the device. There may be two or more modes that are selected, such as a quiet mode, wherein only the light indicator is activated and no audible feedback is provided. Alternatively, an audible mode may be selected and there may be two or more feedback options with the audible mode including, numerical only, melody/song, clean phrases, and/or comical phrases. A user may select one of the desired feedback options. In a numerical only, a numerical value related to the amount of pressure or compression sensed by the device is emitted by the speaker. In a melody/song mode, a song or melody related to the amount of pressure or compression sensed by the device is emitted by the speaker. In a clean phrase mode, only clean phrases related to the amount of pressure or compression sensed by the device are emitted by the speaker. In a comical phrases mode, phrases that might be more humorous and related to the amount of pressure or compression sensed by the device are emitted by the speaker.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS THE DRAWINGS

The accompanying drawings are included to provide a further understanding of the invention and are incorporated in and constitute a part of this specification, illustrate embodiments of the invention, and together with the description serve to explain the principles of the invention.

FIGS. 1 to 4 show an exemplary Kegel exercise pressure measurement and feedback device (Kegel device) having a sensor portion, a connection conduit, a measurement portion and a feedback portion. The bellows of the measurement portion are expanded to different levels in FIGS. 1 to 4 due to the amount of compression of the bladder in the sensor portion.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has,*" having or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the Invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1:
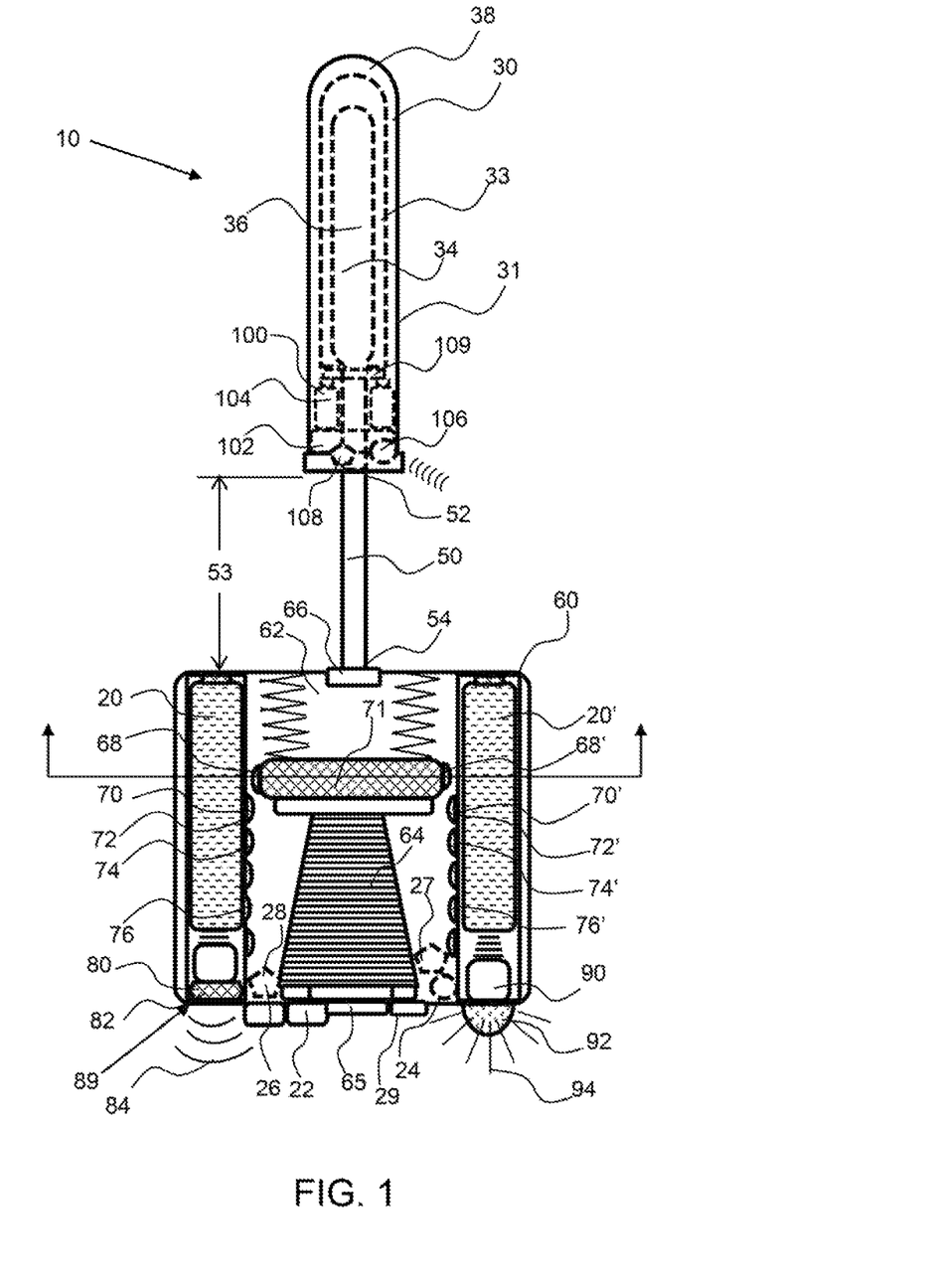
FIG. 1 shows the bellows not expanded and in a ready state.
Figure 2:
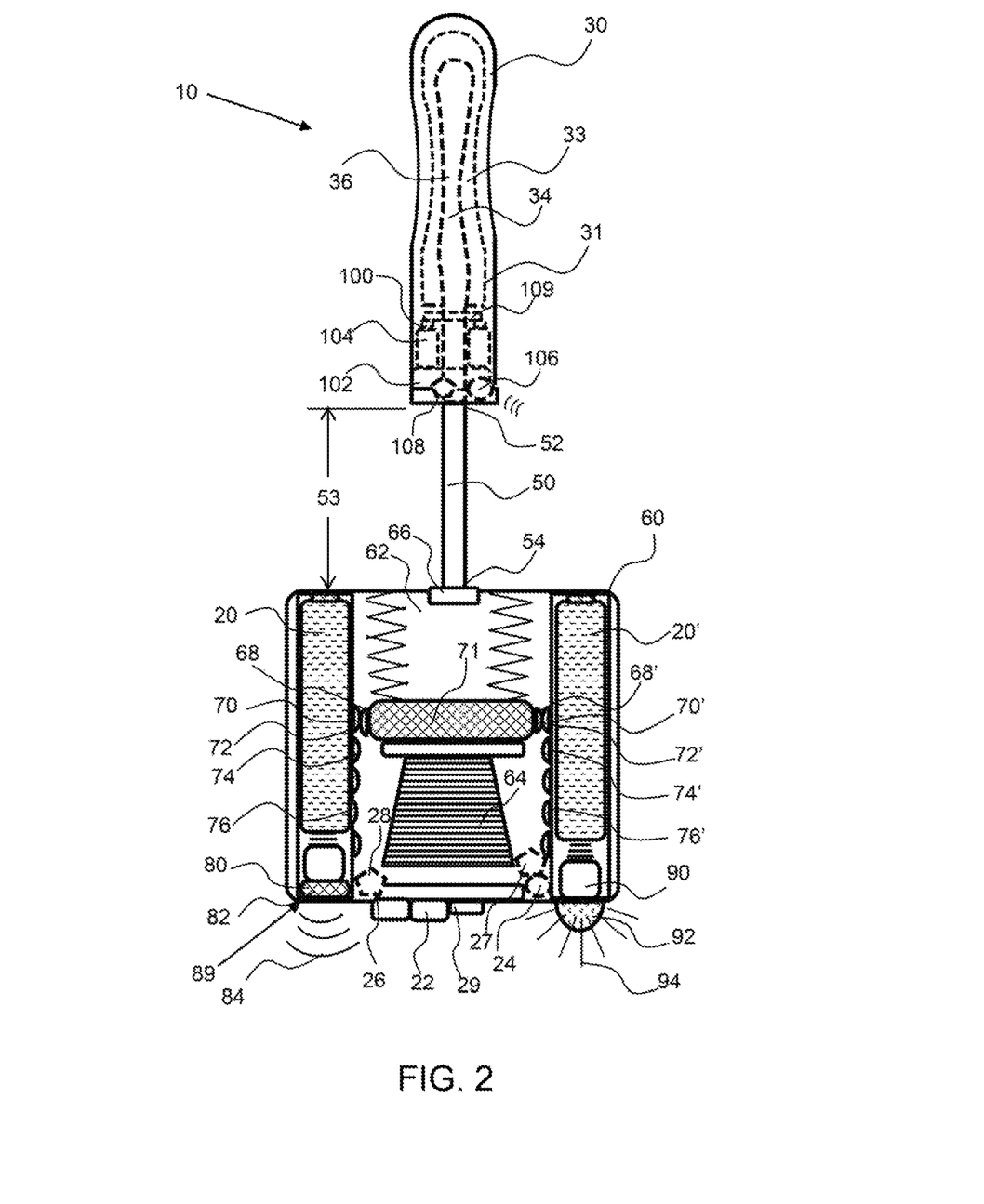
FIG. 2 shows the bladder of the insertion portion compressed and the bellows expanded to locate the bellows contactor in contact with the first level contactor.
Figure 3:
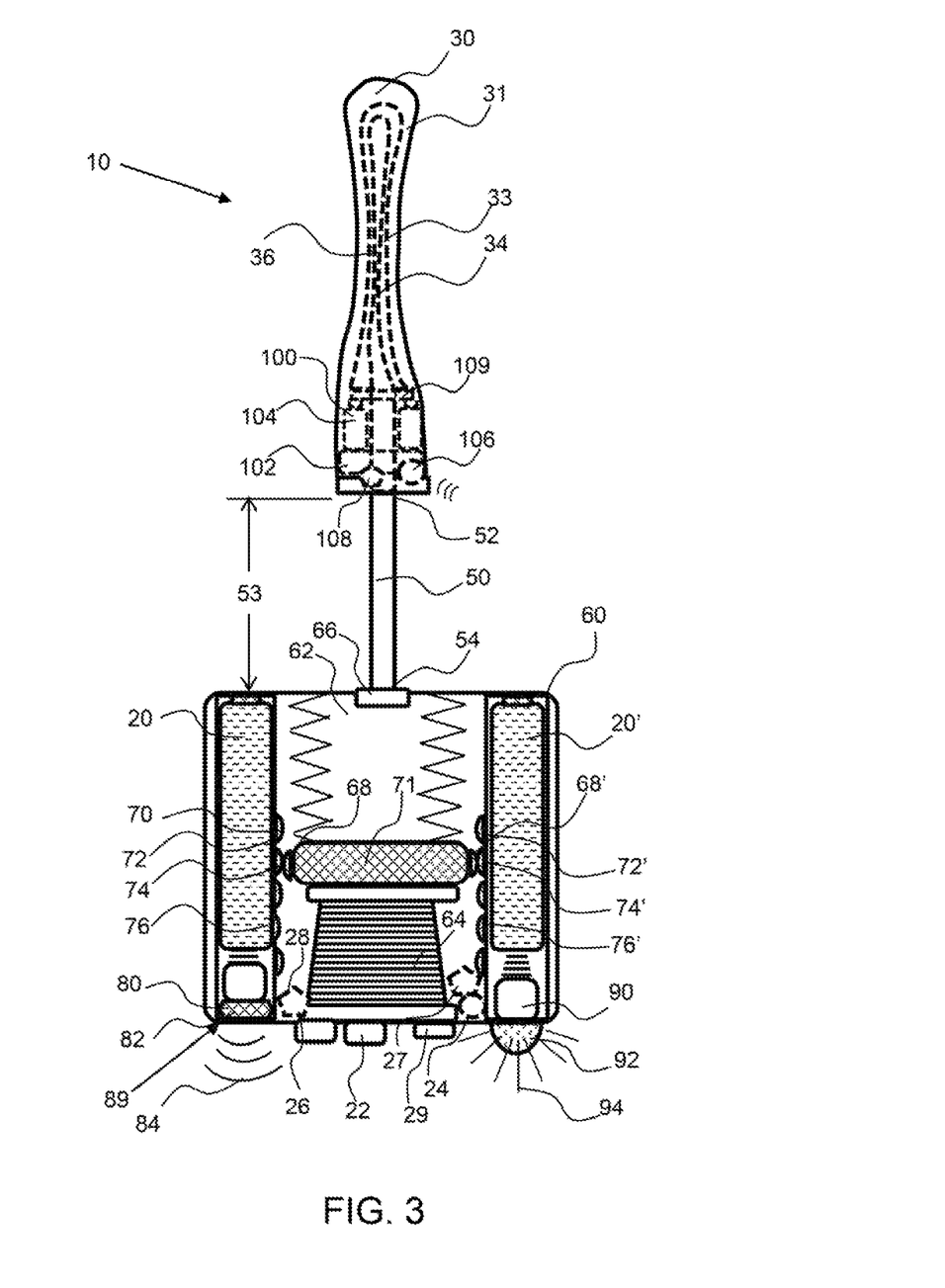
FIG. 3 shows the bladder of the insertion portion compressed further and the bellows expanded to locate the bellows contactor in contact with the second level contactor.
Figure 4:
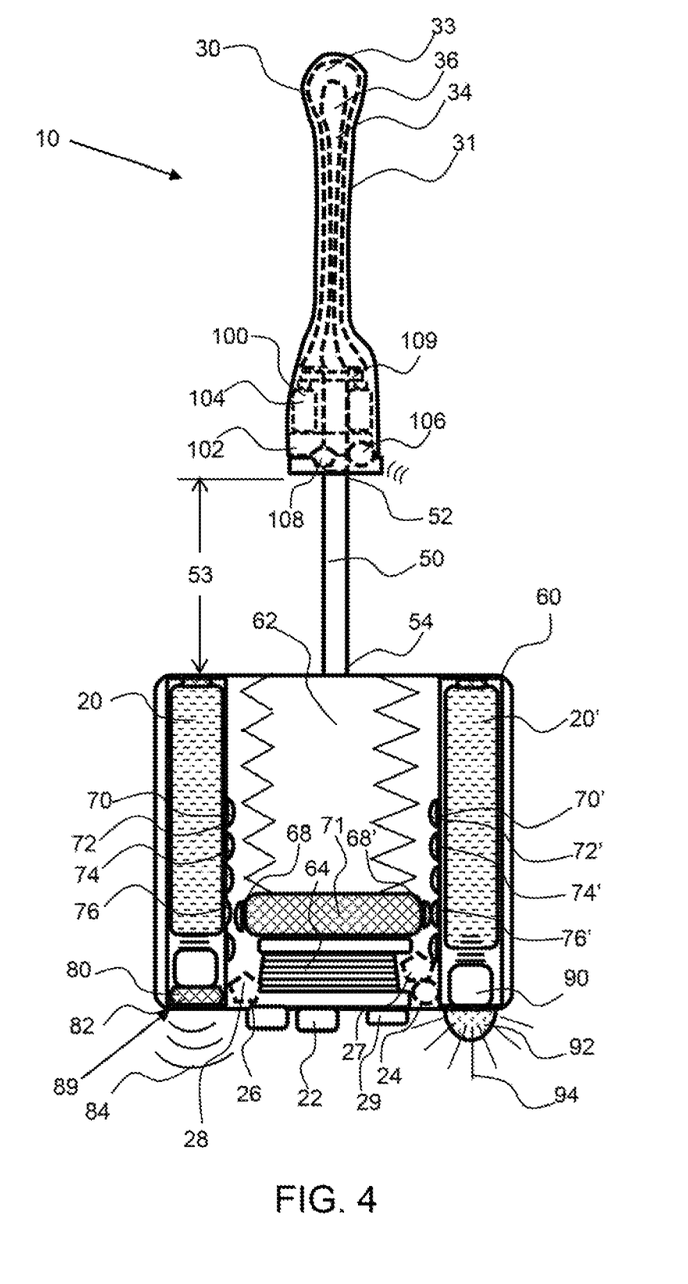
FIG. 4 shows the bladder of the insertion portion compressed even further and the bellows expanded to locate the bellows contactor in contact with the fourth level contactor.

Referring to FIGS. 1 to 5, an exemplary Kegel exercise pressure measurement and feedback device 10 (Kegel device) comprises a sensor portion 30, a connection conduit 50, measurement portion 60 and a feedback portion 89 with the bellows 62 expanded to different levels to create a contact between the bellows contactor 68 and the level contactors 70. The sensor portion 30 comprises a resilient body 31 forming an outer shell 38 around an inner cavity 33. A bladder 34 is configured within the inner cavity and has an internal volume 36. The resilient body is made of a material that is elastomeric and will return substantially to an original shape after being compressed. The outer shell 38 of the resilient body may be interchangeable to allow a user to change the stiffness of the outer shell and therefore change how much compression is required to compress the outer shell and the bladder 34 configured therein. The shape and size of the outer shell may also be changed by a user for their own preferences. A sensor portion configured with a bladder within the inner cavity of the resilient body may enable the outer wall of the resilient body to be thinner and therefore more easily compressed, for example. A woman with more developed Pelvic floor muscles may choose an outer shell 38 that is thicker or stiffer and therefore required more force to compress than a thinner or less stiff outer shell. In addition, a bladder may be sized with an internal volume 36 that will not over expand the bellows 62 and cause damage. The resilient body 31 of the measurement portion may be silicone or urethane, for example. The internal volume is compressed by Kegel exercises, or contraction of the pelvic floor muscles, as shown in FIGS. 2 to 4. The compression of the resilient body 31 compresses the gas, such as air, within the bladder 34 and forces the air through the connection conduit 50 to the feedback portion. The connection conduit has a length 53 from the measurement end 52 to the feedback end 54 and may be a flexible hose, such as a plastic hose. The feedback portion 89 comprises a phrase module 80 that comprises a speaker 82 for emitting a plurality of phrases 84 related to the amount of compression of the measurement portion. An exemplary feedback portion comprises a light module 90, having a light 92 or plurality of lights, that produces an emitted light 94 related to the amount of compression of the measurement portion. An exemplary feedback portion comprises a display 29 that may display a numerical value corresponding to the amount of compression of the bladder.

The measurement portion comprises a bellows 62 that is expanded by the flow of compressed air from the sensor portion 30. When the resilient body 31 is compressed, the bladder 34 is compress and the internal volume 36 is reduced to compress the air therein. The compressed air flows through the connection conduit 50 to the bellows 62 and expands the bellows. A bellows contactor 68, 68' is coupled to the bellows and moves as the bellows is expanded. A plurality of level contactors 70 are configured to contact the bellows contactor as the bellows expands, wherein the first level contactor 72 is contacted first by bellows contactor 68 as the bellows expands and wherein the second level contactor 74 is contacted second by bellows contactor 68 as the bellows expands further. As shown there are five level contactors on opposing sides of the bellows; one to control the phrase module 80 and one to control the light module 90, respectively. A controller 26 may receive input from the level contactors and activate the phrase and/or light modules to activate according to the level of compression of the bladder. The controller may have a short time delay to determine the maximum compression level or contactor level achieved by the bellows contactor before the phrase and/or light module are activated. In this way, the appropriate phrase or light may be emitted according to the compression level achieved.

A controller 26 may control the functions of the Kegel device, such as activating the phrase module 80 to emit a phrase 84, or the light module 90, to emit a light 94, or flashing light. A user interface 22, may allow a user to make selections or to designate a level for a recorded phrase. A user may record a phrase using the microphone 24 and the phrase may be stored in memory 27 on the Kegel device. A user may utilize the user interface 22 to initiate recording of a phrase and to indicate what level the phrase should designated, level one, or level three, for example. The phrase may be stored in memory 27 and emitted by the phrase module 80 when the bellows contactor makes contact with the associated level contactor, as described herein The controller 26 may incorporate a microprocessor 28 for running an algorithm or program that controls the functions of the Kegel device.

A user interface 22 may enable a user to select the type of feedback that is produced by the device. There may be two or more modes that are selected, such as a quiet mode, wherein only the light indicator is activated and no audible feedback is provided. Alternatively, an audible mode may be selected and there may be two or more feedback options with the audible mode including, numerical only, melody/song, clean phrases, and/or comical phrases. A user may select one of the desired feedback options. In a numerical only, a numerical value related to the amount of pressure or compression sensed by the device is emitted by the speaker. In a melody/song mode, a song or melody related to the amount of pressure or compression sensed by the device is emitted by the speaker. In a clean phrase mode, only clean phrases related to the amount of pressure or compression sensed by the device are emitted by the speaker. In a comical phrases mode, phrases that might be more humorous and related to the amount of pressure or compression sensed by the device are emitted by the speaker The exemplary sensor portion 30 of the Kegel device 10 comprises a bladder 34 within an inner cavity 33 of a resilient body 31. When the resilient body is compressed, the bladder is compressed and the air within the internal volume 36 of the bladder is forced out of the bladder, through the connection conduit 50 and into the bellows 62 of the measurement portion 60. The connection conduit has a length 53 from an insertion end 52 to the feedback end 54.

The Kegel device 10 may be powered by one or more batteries 20, 20'. The batteries are required in the measurement device only and therefore are always external from the user, whereas the sensor portion 30 is inserted internal for measurement of Kegel exercise force.

As shown in FIG. 1, the bladder 34 of the measurement portion 30 is not compressed and the bellows contactor is not in contact with any of the level contactors. A spring 64 keeps the bellows compressed and also returns the bellows to a ready state, as shown in FIG. 1, when there is no compression of the bladder 34. A spring tension device 65 enables tensioning of the spring to make expansion of the bellows require more pressure and therefore require more compression of the bladder to move the contactor plate and level contactors attached thereto. An exemplary spring tension device may comprise a threaded portion that interfaces with threads of the housing of the measurement portion, whereby a user can rotate the spring tension device to actuate it into or out of the measurement portion 60. A contactor plate 71 is configured between the bellows 62 and spring 64 and has bellows contactors 68, 68' that contact the level contactors 70, 70, respectively as the bellows expands. There are a series of level contactors including a first level contactor up to a fifth level contactor as shown. The bellows contactor makes contact with the level contactors as the bladder is compresses. A mild or weak compression of the bladder will result in the bellows expanding partially and the bellows contactor contacting the first level contactor 72 or second level contactor 74. When the bellows is compressed to a high degree, the bellows contactor may make contact with the fourth 76 level contactor or the highest level contactor, such as the fifth contactor, as shown in this embodiment. Any number of level contactors may be configured in series, such as two or more, three or more, five or more and even eight or more.

Also shown in FIGS. 1 to 5 is a vibratory feedback module 100 that provides a vibration stimulus to the sensor portion 30 as a function of the amount of compression of the resilient body. The exemplary vibratory feedback module 100 comprises a vibration device 102, such as a piezoelectric device, battery 104, a controller 108, and a wireless signal receiver 106 and/or a vibration sensor 109. The vibration feedback module 100 may provide vibration stimulus when a threshold level of compression is reached or may provide stimulation that corresponds with an amount of compression or force exerted on the sensor portion. An exemplary vibration feedback module may receive sensor input regarding the amount of compression of the resilient body from a separate vibration sensor 109 that is configured with the sensor portion, such as within the resilient body 31 or may receive a signal from the feedback module or measurement portion through a wireless signal receiver 106. The controller 108 of the vibration feedback module 100 may control the level of vibration based on the signals received from the vibration sensor or from the feedback module or measurement portion. This vibration stimulus may encourage a user to strengthen their pelvic floor muscles in an effort to increase this feedback stimulus.

As shown in FIG. 2, the bladder 34 of the measurement portion 30 is now compressed slightly and the bellows 62 has expanded to place the bellows contactor 68 in contact with the first level contactors 72, 72'. This electrical contact between the bellows contactor and the first level contactor will initiate the phrase module 80 and/or light module 90 to activate. The phrase module 80 may emit a phrase 84 that indicates a low level of compression of the bladder, such as "Try harder." The light module may emit a low intensity of light 94 or low frequency of flashing light to indicate a low level, or first level, of compression of the bladder.

As shown in FIG. 3, the bladder 34 of the measurement portion 30 is now compressed more than as shown in FIG. 2, and the bellows 62 has expanded further to place the bellows contactor 68 in contact with the second level contactors 74, 74'. This electrical contact between the bellows contactor and the second level contactor will initiate the phrase module 80 and/or light module 90 to activate. The phrase module 80 may emit a phrase 84 that indicates an increased level of compression of the bladder over that of the first level, such as "You are gaining on it." The light module may emit an increased intensity of light 94 or higher frequency of flashing light than that of first level to indicate an increased level, or second level of compression of the bladder.

As shown in FIG. 4, the bladder 34 of the measurement portion 30 is now compressed even further than as shown in FIG. 3, and the bellows 62 has expanded further to place the bellows contactor 68 in contact with the fourth level contactors 76, 76'. This electrical contact between the bellows contactor and the fourth level contactor will initiate the phrase module 80 and/or light module 90 to activate. The phrase module 80 may emit a phrase 84 that indicates an increased level of compression of the bladder over that of the first, second and third levels, such as "Wow, you don't want to hurt anybody." The light module may emit an increased intensity of light 94 or higher frequency of flashing light than that of third level to indicate an increased level, or fourth level of compression of the bladder.

Figure 5:
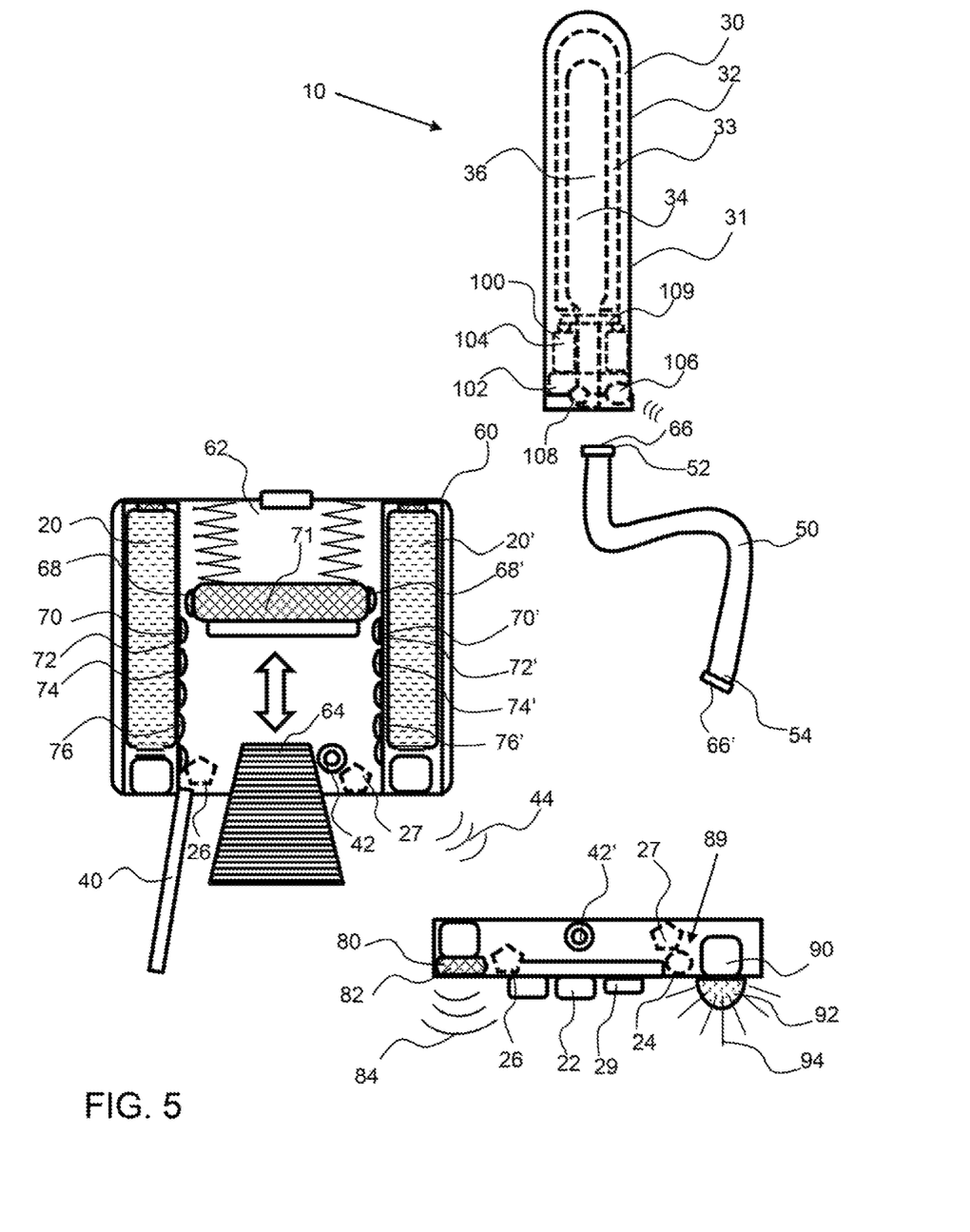
FIG. 5 shows the connection conduit detached from the sensor portion and the measurement portion.

As shown in FIG. 5, the connection conduit 50 is detached from the sensor portion 30 and the measurement portion 60. A conduit connector 66, 66' enables connection of the connection conduit to the sensor portion and measurement portion. The connection conduit 50 and sensor portion 30 may be detachably attachable to the measurement portion for cleaning purposes, for example. The feedback portion 89 is detachably attachable to the measurement portion and is shown as a detached feedback portion. A wireless signal transceiver 42 for transmitting and/or receiving wireless signals 44 is configured on the measurement portion 60. A wireless signal transceiver 42' is configured on the feedback portion 89 to receive signals from the measurement device with level information so that an appropriate phrase from the plurality of phrases can be emitted by the phrase module 80 through the speaker. The feedback portion 89 may comprise a microphone 24 for recording phrases and these phrases may be stored on the feedback module. The detached feedback portion comprises the phrase module and speaker 82, as well as the light module 90 and light 92. An access door 40 may allow a user to change out the spring 64 as required to provide a full range of contact with the level contactors.

Figure 6:
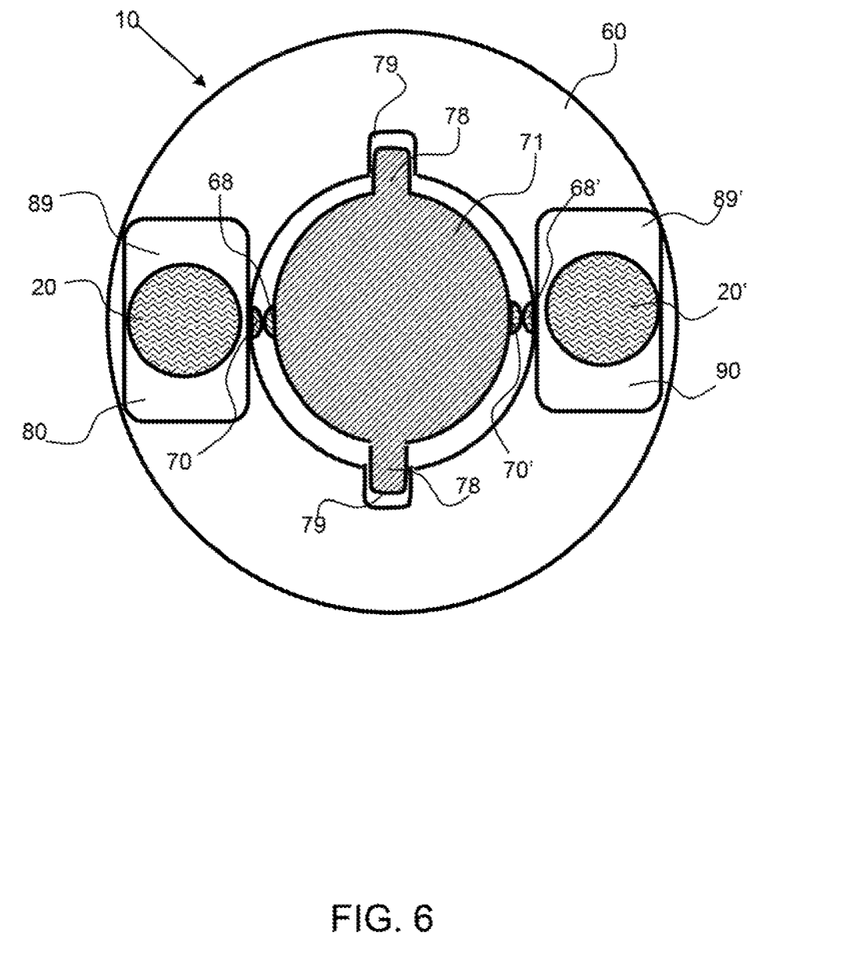
FIG. 6 shows a cross-section view along line 6-6 in FIG. 1.

As shown in FIG. 6, the contactor plate 71, coupled to and between the bellows and the spring, moves within the measurement portion 60 and has tabs 78 that extend into grooves 79 or notches of the measurement portion to prevent the contactor plate from rotating or tilting. This arrangement ensures that the level contactor 70 and the bellows contactor 68 remain aligned as the contactor moves due to the expansion and contraction of the bellows. It is to be noted that the contactor plate may have notches or a recess such as a groove for moving along a tab extending from the measurement portion.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A Kegel exercise pressure measurement and feedback device comprising:
    a) a sensor portion comprising:
        i) a bladder having an internal volume;
    wherein the internal volume of the bladder is configured to be compressed by pelvic floor muscle contraction;
    b) a connection conduit;
    c) a measurement portion comprising:

i) a bellows for receiving compressed air from the bladder through the connection conduit;
  wherein the bellows expands as the compressed air is received from the bladder;
    ii) a bellows contactor coupled to the bellows;
    iii) a plurality of level contactors configured to electrically contact the bellows contactor as the bellows expands; and
  d) a feedback portion comprising:
    i) a speaker that emits a plurality of phrases;
  wherein a first phrase is emitted when the bellows contactor contacts a first level contactor, from the plurality of level contactors, and wherein a second phrase is emitted when the bellows contactor contacts a second level contactor, from the plurality of level contactors;
  wherein the first level contactor is contacted by the bellows contactor before the second level contactor as the bellows expands;
  wherein the connection conduit extends between the bladder and the feedback portion; and
  wherein the first phrase indicates a lower level pressure than said second phrase.

2. The Kegel exercise pressure measurement and feedback device of claim 1, wherein the sensor portion is elongated having a length that is at least two times a width.

3. The Kegel exercise pressure measurement and feedback device of claim 1, wherein the sensor portion is made of an elastomer sensor portion that expands automatically after being compressed.

4. The Kegel exercise pressure measurement and feedback device of claim 1, wherein the sensor portion comprises an inner cavity formed by an outer shell of a resilient body and wherein the bladder is configured within the inner cavity.

5. The Kegel exercise pressure measurement and feedback device of claim 1, wherein the sensor portion is detachably attachable to the measurement portion.

6. The Kegel exercise pressure measurement and feedback device of claim 1, wherein the plurality of level contactors includes three or more level contactors.

7. The Kegel exercise pressure measurement and feedback device of claim 1, further comprising:
    a microphone for recording a recorded phrase that is one of said plurality of phrases; and
    a user interface to save the recorded phrase as the first phrase or second phrase.

8. The Kegel exercise pressure measurement and feedback device of claim 1, wherein the feedback portion is detachably attachable to the measurement portion.

9. The Kegel exercise pressure measurement and feedback device of claim 1, comprising:
    a) a feedback display; and
    b) a user interface having an audible and quiet mode selection,
    wherein in said quiet mode, only the feedback display is activated to display a numerical value corresponding to an amount of compression of the bladder.

10. The Kegel exercise pressure measurement and feedback device of claim 1, further comprising a light module that is illuminated when the bellows contactor contacts one of said plurality of level contactors.

11. The Kegel exercise pressure measurement and feedback device of claim 10, wherein the light module has a plurality of intensity output settings and wherein light is emitted at a lower intensity output when the bellows contactor contacts the first level contactor and is emitted at a higher intensity output when the bellows contactor contacts the second level contactor.

12. The Kegel exercise pressure measurement and feedback device of claim 10, comprising a user interface having an audible mode selection and a quiet mode selection, wherein with the quiet mode scion selected, only the light module is activated to provide feedback.

13. The Kegel exercise pressure measurement and feedback device of claim 12, wherein said audible mode selection has two or more selections comprising a melody mode and a phrase mode song mode; and
    a wherein the phrase mode comprises a melody/song mode; and
    wherein the phrase mode comprises a clean phrase mode.

14. The Kegel exercise pressure measurement and feedback device of claim 1, wherein the feedback portion is separate from the measurement portion and wherein the measurement portion and the feedback portion comprise a wireless signal transceiver for transmitting wireless signals between the measurement portion and the feedback portion.

15. The Kegel exercise pressure measurement and feedback device of claim 1, wherein the measurement portion transmits a pressure level to the feedback portion and wherein the feedback portion emits one of said plurality of phrases that indicates said pressure level.

16. The Kegel exercise pressure measurement and feedback device of claim 1, further comprising:
    a spring coupled to the bellows to produce a force to compress the bellows; and
    a spring tension device coupled to the spring to change said force of said spring.

17. The Kegel exercise pressure measurement and feedback device of claim 1, further comprising a vibration feedback module that produces a vibration stimulus to the sensor portion;
    wherein the vibration feedback module comprises a vibration device.

18. The Kegel exercise pressure measurement and feedback device of claim 17, wherein the vibration feedback module comprises a vibration sensor to measure an amount of compression on the sensor portion; wherein the vibration feedback module produces a vibration stimulus when a threshold compression level is measured by the vibration sensor.

19. The Kegel exercise pressure measurement and feedback device of claim 17, wherein the vibration feedback module comprises a wireless signal receiver for receiving a wireless signal; and
    wherein the vibration feedback module produces said vibration stimulus based on the wireless signal received by the vibration feedback module.

20. The Kegel exercise pressure measurement and feedback device of claim 4, wherein the outer shell of the resilient body is interchangeable.

21. An air pressure measurement and feedback device comprising:
    a) a sensor portion comprising:
      i) a bladder having an internal volume;
    wherein the internal volume of the bladder is configured to be compressed by pelvic floor muscle contraction;
    b) a connection conduit;
    c) a measurement portion comprising:
      i) a bellows for receiving compressed air from the bladder through the connection conduit;
    wherein the bellows expands as the compressed air is received from the bladder;

ii) a bellows contactor coupled to the bellows;
iii) a plurality of level contactors configured to electrically contact the bellows contactor as the bellows expands; and
d) a feedback portion comprising:
i) a speaker that emits a plurality of phrases;
wherein a first phrase is emitted when the bellows contactor contacts a first level contactor, from the plurality of level contactors, and wherein a second phrase is emitted when the bellows contactor contacts a second level contactor, from the plurality of level contactors;
wherein the first level contactor is contacted by the bellows contactor before the second level contactor as the bellows expands;
wherein the connection conduit extends between the bladder and the feedback portion; and
wherein the first phrase indicates a lower level pressure than a second phrase.

* * * * *